United States Patent [19]
Worster et al.

[11] Patent Number: 5,923,430
[45] Date of Patent: *Jul. 13, 1999

[54] METHOD FOR CHARACTERIZING DEFECTS ON SEMICONDUCTOR WAFERS

[75] Inventors: Bruce W. Worster, Saratoga; Ken K. Lee, Los Altos, both of Calif.

[73] Assignee: Ultrapointe Corporation, San Jose, Calif.

[ * ] Notice: This patent is subject to a terminal disclaimer.

[21] Appl. No.: 08/794,673

[22] Filed: Feb. 3, 1997

Related U.S. Application Data

[63] Continuation of application No. 08/497,162, Jun. 30, 1995, abandoned, which is a continuation-in-part of application No. 08/080,014, Jun. 17, 1993, Pat. No. 5,479,252.

[51] Int. Cl.$^6$ .................................................. G01N 21/88
[52] U.S. Cl. .......................... 356/394; 356/448; 356/237
[58] Field of Search .................................. 356/237, 229, 356/388, 392, 393, 394, 430, 448

[56] References Cited

U.S. PATENT DOCUMENTS

| | | | |
|---|---|---|---|
| H1530 | 5/1996 | Lee | 395/124 |
| Re. 34,214 | 4/1993 | Carlsson et al. | 358/93 |
| 4,111,557 | 9/1978 | Rottenkolber et al. | 356/168 |
| 4,247,203 | 1/1981 | Levy et al. | 356/398 |
| 4,333,838 | 6/1982 | Ballnus | 210/614 |
| 4,347,001 | 8/1982 | Levy et al. | 356/398 |
| 4,448,532 | 5/1984 | Joseph et al. | 356/394 |
| 4,455,485 | 6/1984 | Hosaka et al. | 250/234 |
| 4,532,650 | 7/1985 | Wihl et al. | 382/8 |
| 4,549,204 | 10/1985 | Bertero et al. | 358/93 |
| 4,555,798 | 11/1985 | Broadbent, Jr. et al. | 382/8 |
| 4,556,317 | 12/1985 | Sandland et al. | 356/237 |
| 4,579,455 | 4/1986 | Levy et al. | 356/394 |
| 4,604,910 | 8/1986 | Chadwick et al. | 74/96 |
| 4,618,938 | 10/1986 | Sandland et al. | 364/552 |
| 4,633,504 | 12/1986 | Wihl | 382/54 |
| 4,639,587 | 1/1987 | Chadwick et al. | 250/201 |

(List continued on next page.)

OTHER PUBLICATIONS

Technical Brief, "The KLA SAT", KLA Instruments Corporation, Wafer Inspection Division, 1996 (2 pages).
Gonzalez, et al., "Digital Image Processing", Addison–Wesley Publishing Company, 1992, pp. 185–187 and pp. 447–456.
"Working Together", Knights Technology, Inc., Nov. 1995 (8 pages).
"The Yield Manager System", Knights Technology, Inc., Apr. 1996 (4 pages).
"Merlin's Framework", Knights Technology, Inc., Jul. 1997 (4 pages).
"Knightline", Knights Technology, Inc., Winter 1995 (6 pages).
"Knightline", Knights Technology, Inc., Spring 1996 (4 pages).
"Techniques for Syntactic Analysis of Images with Application for Automatic Visual Inspection", Youling Lin, M.S., *A Dissertation in Business Administration*, Dec. 1990.

(List continued on next page.)

*Primary Examiner*—David B. Hardy
*Attorney, Agent, or Firm*—Skjerven, Morrill, MacPherson, Franklin & Friel; Alan H. MacPherson; Gary J. Edwards

[57] ABSTRACT

A method is described for characterizing defects on a test surface of a semiconductor wafer using a confocal-microscope-based automatic defect characterization (ADC) system. The surface to be tested and a reference surface are scanned using a confocal microscope to obtain three-dimensional images of the test and reference surfaces. The test and reference images are converted into sets of geometric constructs, or "primitives," that are used to approximate features of the images. Next, the sets of test and reference primitives are compared to determine whether the set of test primitives is different from the set of reference primitives. If such a difference exists, then the difference data is used to generate defect parameters, which are then compared to a knowledge base of defect reference data. Based on this comparison, the ADC system characterizes the defect and estimates a degree of confidence in the characterization.

25 Claims, 3 Drawing Sheets

U.S. PATENT DOCUMENTS

| | | | |
|---|---|---|---|
| 4,644,172 | 2/1987 | Sandland et al. | 250/548 |
| 4,758,094 | 7/1988 | Wihl et al. | 356/394 |
| 4,786,170 | 11/1988 | Groebler | 356/318 |
| 4,805,123 | 2/1989 | Specht et al. | 364/559 |
| 4,818,110 | 4/1989 | Davidson | 356/358 |
| 4,845,373 | 7/1989 | Jamieson et al. | 250/548 |
| 4,845,558 | 7/1989 | Tsai et al. | 358/106 |
| 4,877,326 | 10/1989 | Chadwick et al. | 356/394 |
| 4,926,489 | 5/1990 | Danielson et al. | 382/8 |
| 4,957,367 | 9/1990 | Dulman | 356/394 |
| 5,030,008 | 7/1991 | Scott et al. | 356/394 |
| 5,032,735 | 7/1991 | Kobayashi et al. | 356/394 |
| 5,112,129 | 5/1992 | Davidson et al. | 356/359 |
| 5,129,010 | 7/1992 | Higuchi et al. | 356/376 |
| 5,243,406 | 9/1993 | Ando et al. | 356/394 |
| 5,280,542 | 1/1994 | Ozeki et al. | 356/375 |
| 5,355,212 | 10/1994 | Wells et al. | 356/394 |
| 5,438,413 | 8/1995 | Mazor et al. | 356/363 |
| 5,438,417 | 8/1995 | Busch et al. | 356/394 |
| 5,448,364 | 9/1995 | Moran | 356/430 |
| 5,465,145 | 11/1995 | Nakashige et al. | 356/237 |
| 5,502,306 | 3/1996 | Meisburger et al. | 250/310 |
| 5,537,669 | 7/1996 | Evans et al. | 382/141 |
| 5,563,702 | 10/1996 | Emery et al. | 356/73 |
| 5,572,598 | 11/1996 | Wihl et al. | 382/144 |
| 5,578,821 | 11/1996 | Meisberger et al. | 250/310 |
| 5,583,632 | 12/1996 | Haga | 356/237 |
| 5,621,532 | 4/1997 | Ooki et al. | 356/444 |
| 5,627,646 | 5/1997 | Stewart et al. | 356/237 |
| 5,671,056 | 9/1997 | Sato | 356/394 |
| 5,680,207 | 10/1997 | Hagiwara | 356/237 |

OTHER PUBLICATIONS

"Integration of Automated Defect Classification Into Integrated Circuit Manufacturing", Louis Breaux, James Kawski and Baljit Singh, *IEEE/SEMI Advanced Semiconductor Manufacturing Conference*, 1994, pp. 290–292.

Frederick Y. Wu et al., "Automated Classification Of Defects In Integrated Circuit Manufacturing," IBM T.J. Watson Research Center, Yorktown Heights, New York, p. 109.

Alan Bearden et al., "Imaging and Vibrational Analysis with Laser–Feedback Interferometry," Opt. Lett., Nov. 6, 1992, pp. 1–14.

METHOD FOR CHARACTERIZING DEFECTS ON SEMICONDUCTOR WAFERS

This application is a continuation of application Ser. No. 08/497,162, filed Jun. 30, 1995, now abandoned, which is a CIP of Ser. No. 08/080,014, now U.S. Pat. No. 5,479,252, filed Jun. 17, 1993.

CROSS-REFERENCES TO RELATED APPLICATIONS

The present application is a continuation-in-part of commonly-owned application Ser. No. 08/080,014 filed on Jun. 17, 1993, entitled "Laser Imaging System For Inspection and Analysis of Sub-Micron Particles," by Bruce W. Worster, Dale E. Crane, Hans J. Hansen, Christopher R. Fairley, and Ken K. Lee now U.S. Pat. No. 5,479,252 issued Dec. 26, 1995. The present application is related to the following commonly owned, U.S. Patent Applications:

1. "A Method and Apparatus for Performing an Automatic Focus Operation," by Timothy V. Thompson, Christopher R. Fairley, and Ken K. Lee, application Ser. No. 08/183,536, filed on Jan. 18, 1994, now U.S. Pat. No. 5,483,055 issued Jan. 9, 1996.
2. "A Method and Apparatus for Automatic Focusing of a Confocal Laser Microscope," by Christopher R. Fairley, Timothy V. Thompson, and Ken K. Lee, application Ser. No. 08/373,145, filed on Jan. 17, 1995, now U.S. Pat. No. 5,672,861 issued Sep. 30, 1997.
3. "Surface Extraction from a Three-Dimensional Data Set," by Ken K. Lee, application Ser. No. 08/079,193, filed on Jun. 17, 1993, now Statutory Invention Reg. No. H00153, issued May 7, 1997.
4. "Surface Data Processor," by Abigail A. Moorhouse, Christopher R. Fairley, Phillip R. Rigg, and Alan Helgesson, application Ser. No. 08/198,751, filed on Feb. 18, 1994, now U.S. Pat. No. 5,557,113 issued Sep. 17, 1996, and
5. "Automated Surface Acquisition For a Confocal Microscope," by Ken Kinsun Lee, application Ser. No. 08/483,234, filled on Jun. 7, 1995, now U.S. Pat. No. 5,594,235 issued Jan. 14, 1997.

These applications are incorporated herein by this reference.

BACKGROUND

Defects in the form of structural flaws, process residues, and external contamination occur during the production of semiconductor wafers. Defects are typically detected by a class of instruments called defect scanners. Such instruments automatically scan wafer surfaces and detect optical anomalies using a variety of techniques. The location of these anomalies with respect to the pattern of semiconductor devices on the wafer surface is recorded. This information, or "defect map," is stored in a computer file and sent to a defect review station.

Using the defect map to locate each defect, a human operator observes each defect under a microscope and characterizes each defect according to type (e.g., particle, pit, scratch, or contaminant). Information gained from this process is used to correct the source of defects, and thereby improve the efficiency and yield of the semiconductor production process. Unfortunately, people are relatively slow and are quickly fatigued by the highly-repetitive task of observing and characterizing defects.

Methods of automatically characterizing defects, collectively known as Automatic Defect Characterization, or "ADC," have been developed to overcome the disadvantages of manual defect characterization. Conventional white-light-microscope-based review stations are automated to load a wafer that has been mapped for defect location by a defect scanner. Once the mapped wafer is loaded, the review station:

1. positions the wafer to image the site of a defect, as indicated by the defect map;
2. focuses on the site of the defect;
3. captures a digital image of the site using a digital TV camera;
4. processes and analyzes the captured image of the site to locate the defect; and
5. further analyzes the data to characterize the defect.

The above process is repeated for each defect (or a predetermined subset of defects) on the wafer. The wafer is then unloaded and the process is repeated for another wafer. By eliminating a fatiguing and highly repetitive task, such automated review stations reduce labor costs and provide improved consistency and accuracy over human operators.

Conventional ADC systems capture a conventional white-light microscope image as an array A representing a two-dimensional image. The image is an x-y array of n by m pixels, where typical values might be n=640, m=480, or n=512, m=512. This array may be represented as:

$$A(x, y, Ir, Ig, Ib),$$

where x and y are pixel coordinates, and Ir, Ig, and Ib represent the intensities of the red, green, and blue image components, respectively. Of course, grey scale images may also be used, as may other color schemes, such as those of the YUV and YIQ commercial standard formats. In the case of a gray scale image, a single intensity parameter Ig is used.

In addition to imaging the defect site, at least one reference image $A_{ref}$ is also stored. The reference image may be a previously stored data-base image of a known-good area of the same or a similar die on the same or on a similar wafer, or it may be a specific image taken from, e.g., an adjacent die. The reference image is compared with the image containing the defect. Any differences measured between the two images will indicate the location and extent of the defect.

Multiple reference images are usually required because slight differences in focus position between the reference and test images may cause false discrepancies to appear. In some cases, a separate reference image is not taken, and instead the reference image is a portion of the same image containing the defect, but from a region of the image where no defect occurs. In general, this latter method is faster but less reliable than methods that use a separate reference image, and works only for images containing repetitive structures or patterns.

Several conventional techniques are available to process images for automatic defect characterization. One such technique is described by Youling Lin, M. S., in *Techniques for Syntactic Analysis of Images with Application for Automatic Visual Inspection,* a dissertation in business administration submitted in December of 1990 to the graduate faculty of Texas Tech University in partial fulfillment of the requirements of the degree of doctor of philosophy, which is incorporated herein by this reference.

Lin describes ADC techniques for processing a two-dimensional microscope image. According to Lin, low-level image processing enhances surface features and reduces noise. This process is performed on intensity (gray scale) variations of the image. Lin describes an extreme-median digital filter to accomplish this task.

Next, Lin describes techniques for identifying feature boundaries and converting the boundaries into a list of symbolic geometric "primitives." Suppose, for example, that a surface feature has the shape of a half-circle. Such a feature will have a-boundary shaped approximately like the letter "D." This boundary could be converted into two geometric primitives; a line segment (specified by length and direction) representing the vertical portion of the "D," and an arc (specified by position and radius) representing the curved portion of the letter "D." More complex shapes may be similarly represented using a large number of connected line segments, angles, and arcs.

Symbolic geometric primitive extraction is performed, for example, by statistical comparison of the edge data with a representation of geometric primitives, such as line segments, arcs, or angles. The surface-feature boundary data is replaced with a set of primitives that best describes the boundary.

The preceding steps are performed both for at least one reference image and for a test image. Then, using techniques derived from compiler theory, the set of reference primitives is compared, primitive by primitive, with the set of test primitives. When a discrepancy is encountered between the sets of reference and test primitives, a rule-based expert system notes the discrepancy and continues the comparison. The discrepancies (i.e., the differences between the sets of reference and test primitives) define the location of a defect.

Alternatively, the defect area may be located by overlaying the test and reference images, aligning them by correlation techniques, and subtracting the images one from the other. Defects will show up as areas where the test and reference images have large difference values.

Having identified the location of a defect, the boundaries of the defect are identified and represented by a set of primitives in the manner described above for the test and reference images. In one embodiment, where more than one defect is located in a single image, only the defect with the largest area is selected for further processing.

Next, the set of primitives representing the image portion containing the defect is used to develop a set of defect parameters, each defect parameter representing a single feature of the defect. For example, one defect parameter may represent the area of the defect and another the shape of the defect. Moreover, characteristics of the area defined by the defect boundaries may be used to derive additional defect parameters. For example, the defect area may be analyzed for average intensity, variations in intensity from one pixel to the next or within a small region ("texture" ), color, or color coordinates. The defect parameters are conventionally expressed in a normalized form so that they run from, e.g., 0 to 1 or −1 to 1. A defect-parameter vector is then defined by these parameters.

The defect-parameter vector is compared, using conventional fuzzy logic techniques, with typical vectors for each known type of defect. Based on this comparison, the ADC system characterizes the defect and estimates the probability that the selected characterization is accurate. For a more detailed description of one method of developing a defect-parameter vector, see *Techniques for Syntactic Analysis of Images with Application for Automatic Visual Inspection*," which is incorporated herein by reference.

For further discussion of conventional ADC techniques, see the IBM technical disclosure entitled *Automated Classification of Defects in Integrated Circuit Manufacturing*," by Frederick Y. Wu, et al., which is incorporated herein by this reference.

Conventional ADC images have a number of shortcomings. For example, small pits versus particles cannot be distinguished, shallow structures are not discernible, and subsurface defects cannot be characterized. And, if a defect or structure on a surface is "tall," focusing on one level leaves other levels out of focus. Accuracy of the automatic focus between the test and reference image then becomes critical because small variations in focus cause the boundary between two structures of different heights to change in appearance. A conventional ADC system may then interpret this variation as a potential defect when it is not. Human operators can compensate for this to some degree by, e.g., moving the focus up and down and interpreting three-dimensional aspects of the images, but this wastes valuable time. Moreover, if there are low optical contrasts between the defect and the surrounding material (e.g., the defect is of approximately the same color or reflective intensity as the surrounding surface of the semiconductor), an ADC scheme can fail to detect the true shape—or even the existence—of the defect. Therefore, what is needed is a more accurate method of automatically characterizing defects.

SUMMARY

The present invention involves Automatic Defect Characterization (ADC) with a resulting improved accuracy and efficiency over the prior art. In one embodiment, ADC is based on three-dimensional data, including white-light confocal images and laser-based confocal images. The present invention also involves further extension of these techniques to Laser Feedback Microscopy (LFM) derived arrays, and "image" arrays developed from other techniques.

In accordance with the present invention, a test surface is defined by a set of points on, the test surface, the set of points being described by a Cartesian coordinate system having x, y, and z axes such that each point has a unique location described by x, y, and z coordinates.

To so define the test surface, the test surface is contained with a rectangular test volume described by the x, y, and z axes used to define the test surface. The rectangular test volume contains a superset of test points defined by incremental x, y, and z coordinates. Using confocal optics, the test volume is scanned by a focussed beam of light so that the focal point of the beam coincides, in turn, with each point within the test volume. The intensity of reflected light returned for each point in the test volume is measured to obtain a data value representing the reflected intensity for that point.

Next, the Z value that resulted in a maximum reflected intensity value is determined for each column of z values (each represented by a unique x, y coordinate in the test volume). In accordance with the principles of confocal optics, the measured intensity of reflected light is greatest when the focal point of the beam is coincident with the surface. Therefore, the Z value that resulted in a maximum reflected intensity value for a given column of z values indicates the location of the surface point along the z axis (i.e., the elevation of the point).

In addition to the Z value corresponding to the maximum reflected intensity, the ADC system also determines and stores a value representing the maximum reflected intensity of each point.

The maximum reflected intensity value and the location along the z axis of each of the points on the test surface are stored as a set of test data representing a three-dimensional image of the test surface. From this three-dimensional image, the system extracts a set of geometric constructs, or "test primitives," that approximates features of the three-dimensional image of the test surface. This set of test primitives is compared to a set of reference primitives derived from a reference image to determine whether the set of test primitives is different from the set of reference primitives.

Differences between the test and reference primitives indicate the presence of a defect. When such differences exist, the ADC system generates a set of defect parameters from the differences between the set of test primitives and the set of reference primitives. The defect parameters define a defect-parameter vector, which is matched with a knowledge base of reference defect-parameter vectors to determine the type of defect.

DETAILED DESCRIPTION

I. Three Dimensional Laser Confocal Surface Image ADC

Figure 1:
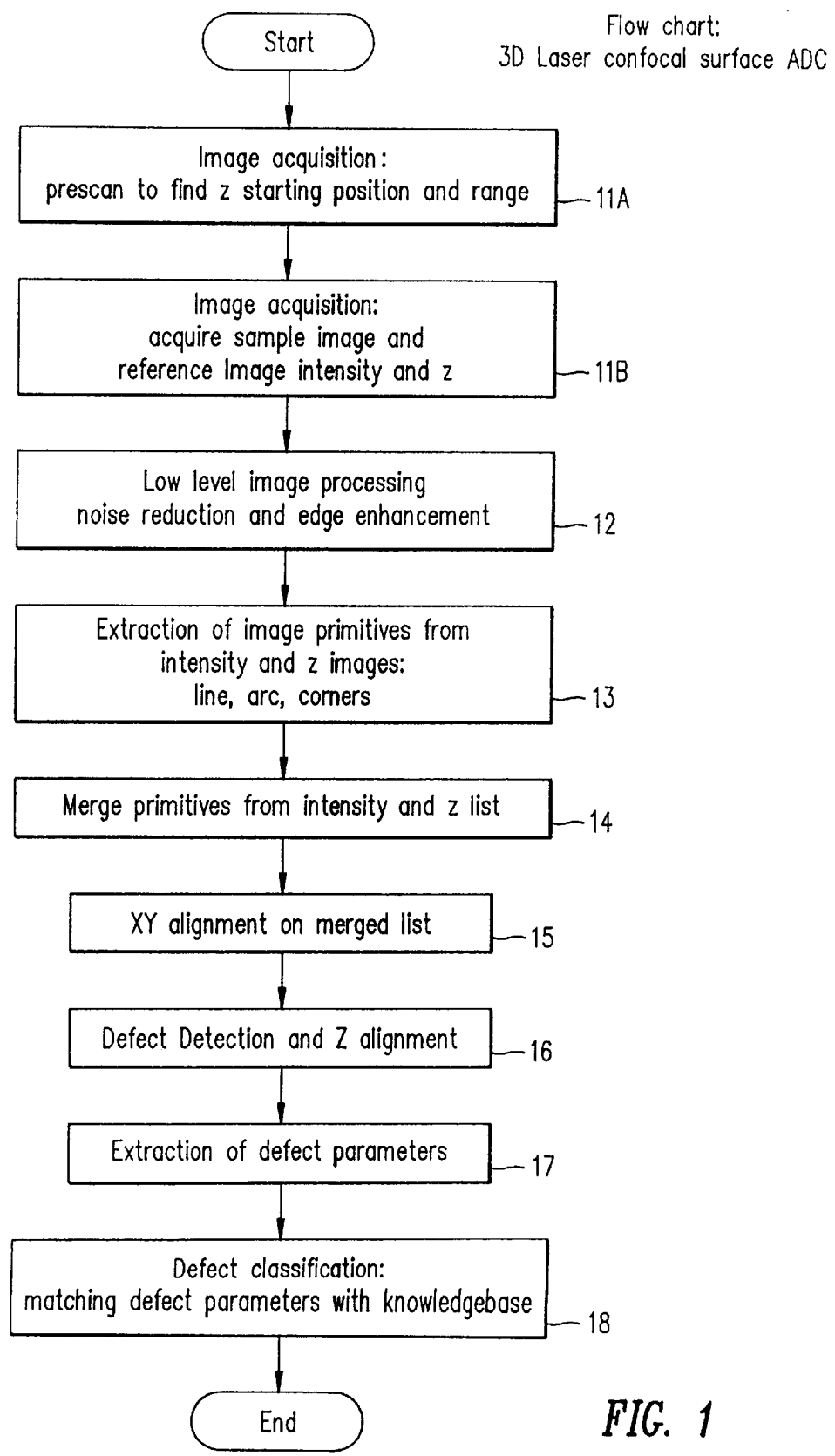
FIG. 1 is a flow chart that depicts the process of characterizing defects using a three-dimensional surface image in accordance with a first embodiment of the invention.

FIG. 1 is a flow chart that depicts the process of characterizing defects using a three-dimensional surface image obtained using a laser imaging system (LIS) in accordance with a first embodiment of the invention. (An LIS in accordance with the present invention is described in the above-identified patent application entitled "Laser Imaging System For Inspection and Analysis of Sub-Micron Particles," incorporated herein by reference.) Once the ADC process is initiated, the process begins at Step 1, "Image Acquisition."

Steps 1A and 1B: Image acquisition

Images of a test surface and at least one reference surface are obtained using a confocal microscope, preferably a laser-based confocal microscope. The following describes the process of obtaining an image using a confocal microscope, and is applicable to both test and reference images.

Beginning at Step 1A, to ensure the correct settings of the z starting position and the z range, a preliminary scan is taken prior to the capturing of the test or reference image to determine the optimal z starting position and z range. The starting position and the z range are important. If the first surface scan begins too far above or below the surface of interest, the image slices may not cover the defect. If the range is too large, defects may be captured with insufficient resolution in the z direction. In one embodiment, this preliminary scan is accomplished using the set-Z function described in the above-identified application entitled "Automated Surface Acquisition For a Confocal Microscope," which is incorporated by reference.

Next, at Step 1B the LIS generates an image of the test surface using a confocal microscope. To obtain an image of a surface using a confocal microscope, a beam of light passes through an objective lens and is scanned across the test surface from a number locations along a z axis. At each z location, the scanned laser beam generates a number of signals, each of the signals representing an intensity of light reflected through the objective lens from a given point on the surface. The group of signals provided by an x-y scan from a single z location of the objective lens is called a "slice" of intensity data. Slices taken from a number of locations along the z axis overlap to form a three-dimensional set of reflected intensity data, hereafter referred to as a "volumetric data set."

The overlapping slices of data create a column of data values for each point on the surface, each data value representing a reflected intensity of light from that point from a particular Z location. For each such column, data values are compared to determine the location along the z axis that resulted in a maximum reflected intensity. Because the intensity of the reflected light from a particular point is greatest when that point on the surface is coincident with the focal plane of the objective lens, the location of the objective lens on the z axis that corresponds to the maximum reflected intensity gives an indication of the z coordinate of that point on the surface. In this way, the x, y, and z Cartesian coordinates are determined for each point on the surface. An image of the surface may then be generated from this information.

The volumetric data set from a laser imaging system (LIS) or a white-light confocal microscope may be represented as an array $A(x, y, z, I_\lambda)$. This array contains data representing reflected intensity (i.e., $I_\lambda$) for every x-y-z coordinate scanned. Different plane images P may be derived from the volumetric data set by making cuts through the array, such as a single horizontal slice $P_H$ (x, y, Z, $I_\lambda$), where Z represents a single value of z, or vertical planes such as $P_y(X, y, z, I_\lambda)$ or $P_x(x, Y, z, I_\lambda)$, where X and Y represent single values of x and y, respectively. Other planes may also be specified at any arbitrary orientation to the original x, y, and z axes. In addition to the Cartesian coordinate system described above, other systems, such as those using spherical or cylindrical coordinates, can be used to describe the volumetric data set.

A pair of surface arrays, $S_I$ and $S_Z$, may be derived from a volumetric data set extracted by a confocal microscope by determining, for each x-y coordinate pair, the maximum intensity value, $I_{\lambda max}$, and the Z coordinate corresponding to the maximum intensity value. (For simple reflective surfaces, the confocal response of the LIS is a maximum at the surface.) The surface intensity array $S_I$ may be represented as:

$$S_I(x, y, I_{\lambda max}),$$

and the array of z coordinates corresponding to the maximum intensity values may be represented as:

$$S_Z (x, y, Z_{Imax}),$$

where $Z_{Imax}$ represents the Z coordinate corresponding to the point of maximum reflected intensity for a given x-y coordinate.

In one embodiment, surface arrays $S_I$ and $S_Z$ are updated as the ADC system scans the test surface from each Z position. Each intensity value of each slice of intensity data is compared to a maximum intensity value corresponding to the same x-y coordinate in the array of maximum intensity values. If the intensity value of the slice is greater than the corresponding maximum intensity value, then the intensity value of the array of maximum intensity values, $S_I$ (x, y, $I_{\lambda max}$), is updated with a new maximum intensity value for that x-y coordinate and the array of Z values, $S_Z(x, y, Z_{Imax})$, is updated with the Z location of the new maximum intensity value. Because the point of maximum reflected intensity gives an indication of the location of the surface, the array of Z values provides an indication of the surface contour. This second method is faster and requires less memory than is required for generating a complete volumetric data set.

For a more detailed description of a laser imaging system that employs a confocal microscope, see the co-pending application entitled "Laser Imaging System For Inspection and Analysis of Sub-Micron Particles," the content of which is incorporated herein by reference.

The aforementioned embodiments use three-dimensional images, such as surface array $S_Z(x, y, Z_{Imax})$, derived from either a LIS or a white-light confocal microscope, to perform improved ADC. The use of three-dimensional images overcomes the x-y resolution, vertical resolution, and low-contrast problems that limit the performance of conventional ADC systems. It will become apparent to those skilled in the art that the present invention may be used to perform defect detection only, or, alternatively, to perform both defect detection and identification.

Step 2: Low-Level Image Processing

After the test image and reference image are taken using the image extraction method described in connection with Step 1, the images are processed by digital filtering to reduce noise and enhance boundaries. Here "texture" occurs both in intensity contrast and in surface height variations (also expressed as "roughness" or, alternately, "smoothness"). Also, structures are characterized by height differences as well as by contrast differences across structure boundaries. Hence, the filtering must handle both the intensity and the z-dimension values stored in the surface image array. Examples of appropriate filters include conventional low-pass filters, conventional median filters (as described in "*The Image Processing Handbook, Second Edition,*" by John C. Russ, CRC Press, 1995, which is incorporated herein by this reference), and extreme-median filters, as described in "Techniques for Syntactic Analysis of Images with Application for Automatic Visual Inspection."

Step 3: Extraction of Geometric Primitives

The intensity variables of the test image and reference image are processed to locate and reduce the boundaries of surface features. To accomplish this, the test and reference image intensity arrays, which are expressed as $S_I(x, y, I_{\lambda max})$ as discussed above, are subjected to "thresholding and skeletonization," a conventional edge-detection technique. Other edge-detection techniques are commonly available, such as "automatic tracing." These and other edge-detection techniques are detailed in "*The Image Processing Handbook.*" Such detectors are used to define the boundaries of the various surface features. Next, the defined feature boundaries are converted into a list of symbolic primitives that are combined to represent the boundaries. Conventional approaches to extraction of geometric primitives and analysis and characterization of shape boundaries are described in "*Techniques for Syntactic Analysis of Images with Application for Automatic Visual Inspection.*"

Next, the z variables of the test image and reference image are processed to locate and reduce the boundaries of surface features. The test and reference image z arrays, which are expressed as surface arrays in the form $S_z(x, y, Z_{Imax})$ as discussed above, are subjected to a conventional edge-detection technique, such as "automatic tracing" or "thresholding and skeletonization," to define the boundaries of the various surface features. Next, using conventional methods, the defined feature boundaries are converted into a list of symbolic primitives that are combined to represent the boundaries.

Step 4: Merging Intensity and Z Primitives

The two lists of primitives created in the last step are merged into a combined primitive list, so that the combined list of primitives contains information indicative of the size, intensity, orientation, and location in x-y-z space of image features.

Step 5: X-Y Alignment

Using conventional auto-alignment techniques, the merged list of primitives from the test surface is shifted, compared, and matched with a similar list of primitives from the reference image. The x-y offset between test image and reference image is calculated using the x-y locations of the matched primitives. The x-y offset is then used to calculate the overlapping area between test image and the reference image.

Step 6: Defect Detection and Z Alignment

Once aligned, the lists of test and reference image intensity primitives are compared to determine whether differences exist between them. Any difference (e.g., any missing, extra, or misplaced geometric primitives) between the test list and the reference list indicates the presence of a defect.

The z axes of the test and reference surfaces are then aligned by subtracting the lowest z value in the overlapping area (i.e., the area shared by the test and reference arrays where no difference is detected) of the test array from all other z values in the overlapping area of the test array, and subtracting the lowest z value in the overlapping area of the reference array from all other z values in the overlapping area of the reference array. Thus, the lowest z value in the overlapping area of each array is 0, so that absolute height is converted into relative height.

Step 7: Extraction of Defect Parameters

Having identified a defect, defect boundaries are located, using conventional thresholding and skeletonization techniques. The boundaries are then conventionally represented by geometric primitives as described above. Neighboring defect primitives are grouped together and combined with their interior pattern to represent the area defined by the defect in x-y space as a single "high-level" defect.

The surface image provides up to three different lists of parameters for enhanced boundary detection and characterization: the intensity list, the z list, and the merged list of intensity and z lists. In one embodiment, the z list (and consequently the merged list) is not generated unless the intensity contrast of the surface under test is low, resulting in poor intensity image quality. Such selective use can save valuable time. Any two or all three may be used, depending on the desired level of analysis.

Step 8: Defect Characterization

Next, defect parameters are developed by analyzing various characteristics of the defect area as defined by a defect parameter dictionary. Such characteristics include image intensity, texture (i.e., local variations in brightness from one pixel to the next or within a small region), boundary curvature, surface curvature, height (in z), area, and shape. For example, if height is used as a defect parameter, then the height of the defect is assigned a magnitude conventionally expressed in a normalized form so that values run from, for example, 0 to 1 or −1 to 1. Other parameters are similarly assigned magnitudes, and these magnitudes are used to define a defect-parameter vector corresponding to the defect.

Similar defects have similar defect-parameter vectors. In other words, two defects with similar size, shape, texture, surface curvature, etc., will have similar defect-parameter vectors, and are likely to be similar defects. Based on this premise, the present invention characterizes a defect by comparing the defect's defect-parameter vector, using conventional fuzzy-logic comparison techniques, with previously stored defect vectors for different types of defects. The closest vector match is used to characterize the defect. The present invention further estimates the degree of confidence in the characterization based on the precision of the defect-parameter vector match.

For a more exhaustive analysis, additional defect parameters may be obtained by analyzing a vertical slice of data taken through the defect so that the vertical slice represents a vertical, two-dimensional cross-section of the defect. Such a cross-section may be used to define defect parameters representing, for example, cross-sectional area and boundary features.

In another embodiment, additional defect parameters are defined by providing one or more silhouettes of the defect by looking "sideways" at the defect to determine the defect profile. To ensure that only the defect is considered, only those columns of data points (i.e., data points sharing a common x-y location) within the x-y defect boundary are considered.

For example, the defect may be viewed along a line parallel to the x axis from the first y location of defect boundary to the last y location of the defect boundary. Only those data columns that vertically intersect the x-y defect boundary are considered. When looking at the defect from the x direction, the x element of the array is not considered. Therefore, the side view is effectively an infinite-depth-of-focus view of one side of the defect (i.e., a silhouette of the defect). Additional defect parameters, such as profile shape, may be defined by the silhouette. Additional defect parameters may be obtained by providing similar silhouettes from other angles.

Software for performing two-dimensional ADC analogous to the three-dimensional process described with reference to steps 2 through 8 above is available from ISOA, Inc. of Richardson, Texas. However, the software must be modified to accommodate the additional information provided by the z data. Such modifications will be readily understood by those skilled in the art.

Importantly, the availability of z data provides additional defect parameters. These include (1) physical roughness (small z variations) of the defect area, (2) z contrast variations (i.e., large z variations), (3) sign of the relative z value of the defect region compared with the reference, which may be used, for example, to distinguish between pits and particles, (4) actual z values of the defect region relative to the reference, (5) surface slope, determined by relative z values of adjacent x-y location. Moreover, using the defect cross-section and silhouette techniques described above, defect parameters may be developed to represent surface curvature and cross-sectional area.

By adding one or more of the above-listed parameters to the defect vector characterizing a given defect, additional information about the nature of the defect and its relationship to its environment can be obtained. Even small differences in surface height over a limited region with respect to the rest of the image can indicate buried defects of non-trivial thickness that have caused an overlying layer to bulge upward. And, small surface depressions can indicate subsurface voids in prior layers. Because the defect-parameter vector contains additional and unique information, the accuracy of the characterization is improved over two-dimensional ADC, and the number of different defect types that can be characterized is expanded over the conventional microscope image analysis.

II. Top-View Laser Image ADC

Figure 2:
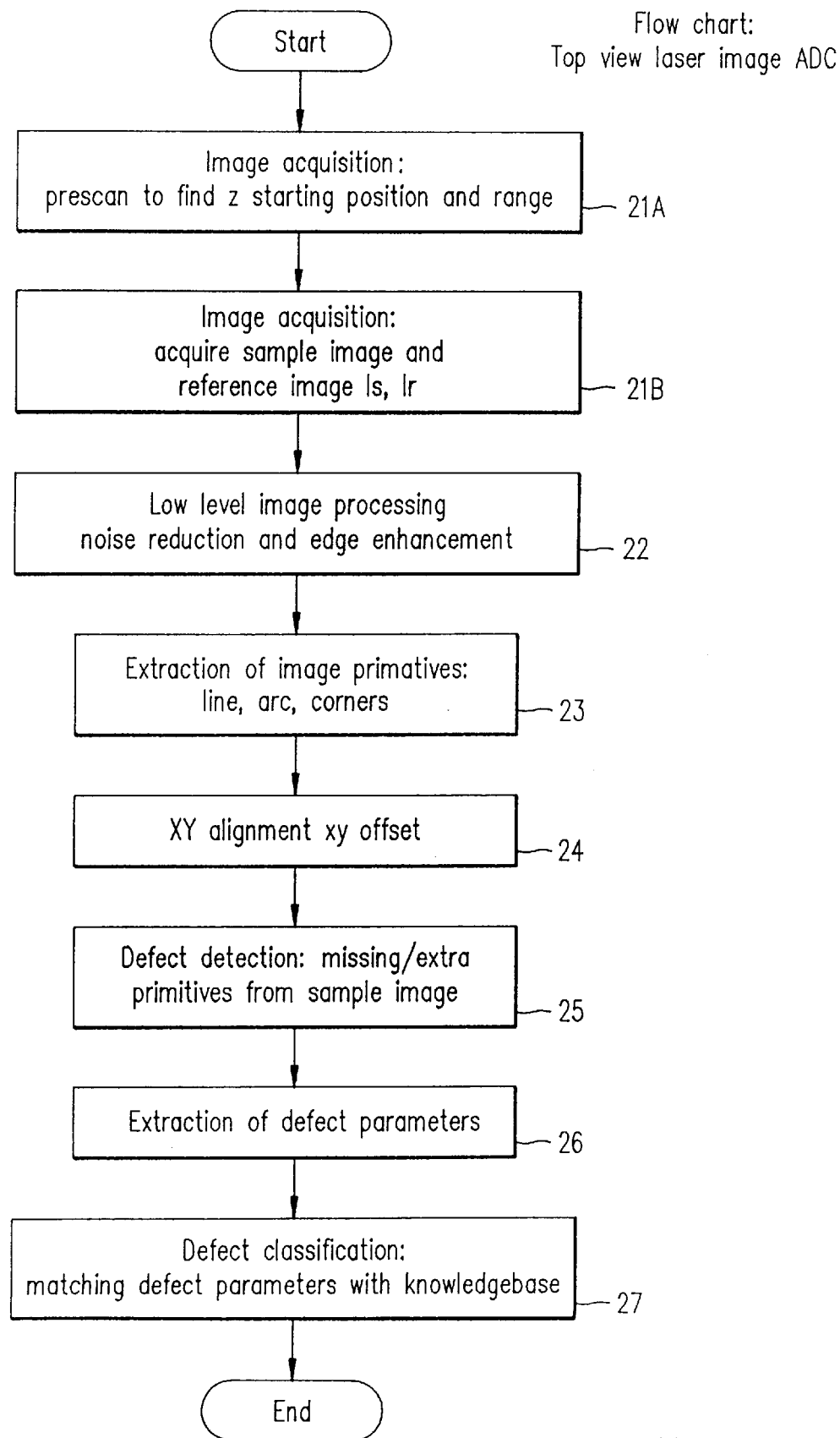
FIG. 2 is a flow chart that depicts the process of characterizing defects using a two-dimensional top-view surface image in accordance with a second embodiment of the invention.

FIG. 2 is a flow chart that depicts the process of characterizing defects using a two-dimensional, top-view surface image in accordance with a second embodiment of the invention.

The three-dimensional surface image array S described above in connection with FIG. 1 may be reduced to image array S' (x, y, $I_{\lambda max}$) by eliminating the z value. Image array S' is the equivalent of an "infinite" depth of field top-view image of the surface (i.e., all points are in focus, regardless of the height). This new image differs from conventional two-dimensional images in that the new image has improved resolution and infinite depth of field. The improved resolution provides more information for ADC analysis. In addition, because surface characteristics that would be out of focus in a conventional image are now in focus, the array S' allows for evaluation of, e.g., texture, without obtaining additional images.

A similar "infinite" depth of focus image, either grey scale or color, can be obtained from a white-light confocal microscope focus exposure series, but chromatic aberration and other resolution limitations of this procedure affect the quality of the result. Still, it would be an improvement over a single conventional image, and could be used in ADC.

The top-view laser image (or top-view confocal image) may be used in place of the conventional video camera image to provide a two-dimensional array with improved resolution and no focus discrepancy problems between test and reference images. Hence, only one defect-free reference image is required for non-repeating pattern images, rather than multiple references to obtain the best focus comparison. For repeating pattern images, the correlation of image characteristics will be more consistent from one sample to the next, resulting in more accurate defect characterization.

Upon initiation of the ADC process, the LIS begins at Step 1A, "Image acquisition." This and the following steps are similar to those described above in FIG. 1 for three-dimensional surface ADC, except that the elimination of the z data simplifies each step of the process and eliminates the step of merging primitives. The two-dimensional data may then be processed to characterize defects using ADC software available from ISOA, Inc. of Richardson, Texas.

III. Three-Dimensional Laser Confocal Volume Image ADC

In the case of opaque surfaces, a three-dimensional surface image obtained using a LIS contains almost as much information as the full-volume image represented by the volumetric data set. However, when viewing transparent or semi-transparent structures, such as dielectric films, a simple surface extraction is often insufficient to obtain a realistic representation of the wafer surface. This is because light from the imaging system can pass through transparent structures to be reflected from subsurface layers. Three-dimensional processing provides an important advantage over conventional ADC systems, which cannot distinguish a large class of defects that are embedded or lie below or within transparent layers.

Figures 3A, 3B:
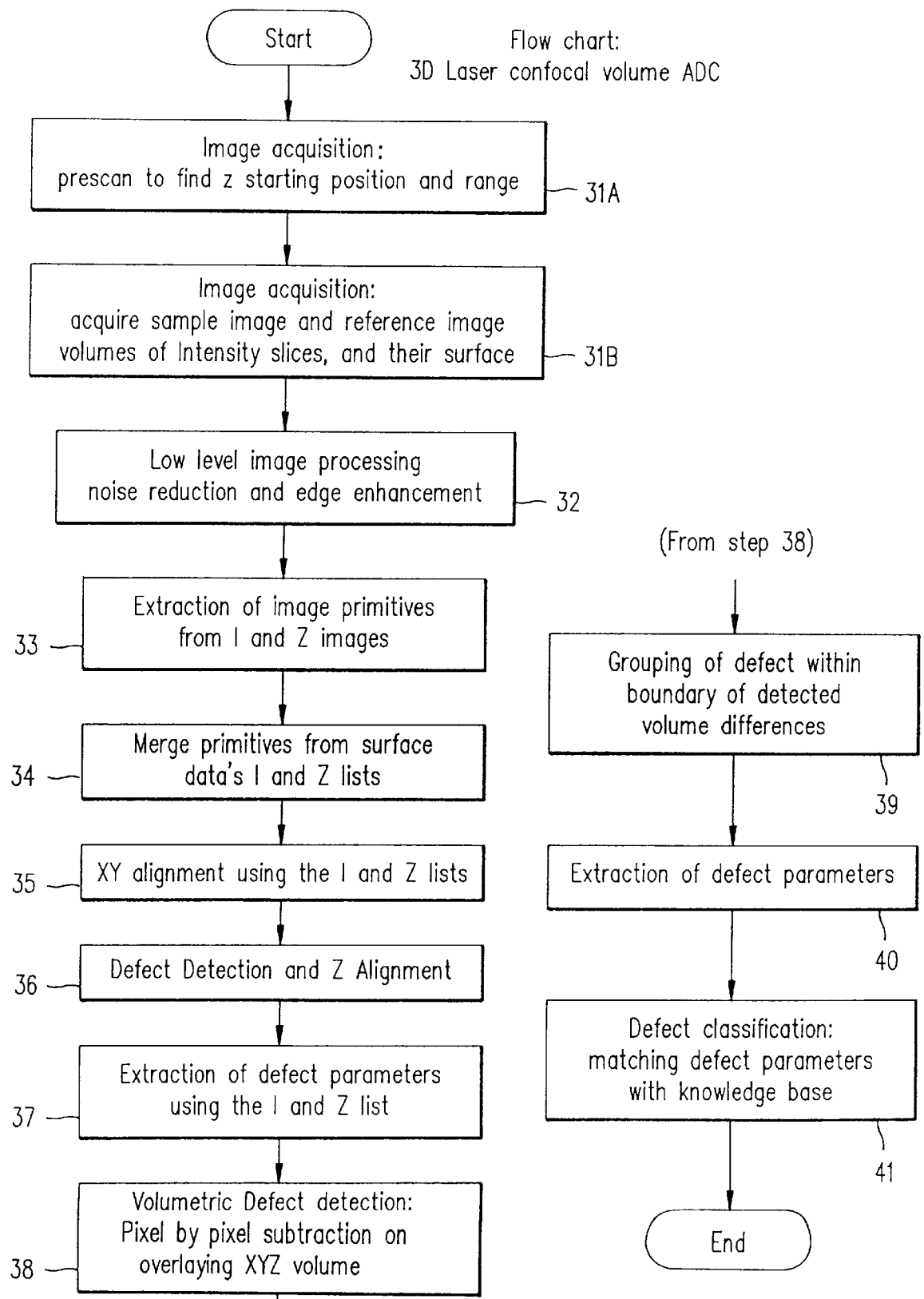
FIGS. 3A and 3B combine to provide a flow chart that depicts the process of characterizing defects using a three-dimensional volumetric data set in accordance with a third embodiment of the invention.

FIGS. 3A and 3B combine to provide a flow chart that depicts the process flow of an ADC system that uses three-dimensional volume imaging in accordance with a third embodiment of the invention. Once the ADC process is initiated, the process begins at Step 1A, "Image Acquisition."

Steps 1A and 1B: Image Acquisition

The set of test images (slices of x-y intensity images), and the set of reference images where needed, are generated in a manner similar to that as described for acquiring the top-view laser image. In this case, the raw, unprocessed slices of data, which make up a volumetric data set, are stored in memory as array $V(x, y, z, I\lambda)$.

Step 2: Low-level image processing

In any column of data points parallel to the z axis (i.e., for fixed values of x and y), the volume image contains the confocal z response of the system convolved with the reflectance of each surface encounter, combined with the absorption and scattering of each layer traversed by the light. Local peaks in intensity appear corresponding to each surface, and intensity is modulated by the reflectivity of each interface, as well as by attenuation of the light during its round-trip through the wafer surface media.

The first order of processing is to sharpen the peaks of intensity corresponding to surfaces. In one embodiment, conventional deconvolution techniques are applied along each column of data points parallel to the any z axis, removing the confocal z response. In another embodiment, conventional deconvolution techniques are applied over a vertical plane cut through the volumetric data set. Finally, conventional deconvolution techniques may be performed in three dimensions, compensating for contributions from surrounding surfaces, and operated over subsets of the volumetric data set large enough to provide good correction but small enough to allow processing in a reasonable time.

Alternately, the peaks of intensity may be sharpened applying conventional two-dimensional sharpening filters to any set of vertical planes cut through the volumetric data set, or by applying conventional one-dimensional sharpening filters along one or more columns (i.e., unique x-y coordinate) of data. This is done to define (1) multiple surfaces within the volumetric data set that delineate multiple layers and elevations of the wafer structure, and (2) the surfaces of any defects.

Steps 3–7

Steps 3–7 of FIG. 3 are performed in much the same way as described above in connection with three-dimensional laser confocal surface image ADC. However, because the volumetric image typically provides an indication of more than one surface, for example a surface underlying a transparent or semitransparent film, a principal surface must be selected for analysis. The principal surface selected is typically the top surface. Also, due to the need for additional volume information, the entire volumetric data sets for the test and reference surfaces must be maintained.

The preceding steps may provide sufficient information to characterize a defect. However, the data obtained may be insufficient to characterize—or even detect—subsurface defects. In one embodiment, if the data obtained through Step 7 is sufficient to characterize a defect with an acceptable degree of accuracy, the ADC system moves directly to Step 11, Defect Characterization.

Step 8: Volumetric Defect Detection

The test and reference intensity data sets are expressed as arrays $V_{test}(x, y, z, I\lambda)$ and $V_{ref}(x, y, z, I\lambda)$, respectively. To find a defect in the volume of the test array $V_{test}$, the data value stored for each voxel (i.e., each x, y, z coordinate) is subtracted from the data value of the corresponding voxel (i.e., the same x-y-z coordinate) of the reference array $V_{ref}$. The location and extent of one or a group of differences indicates the location and extent of a defect. In one embodiment, a difference does not indicated a defect unless the value of the difference data exceeds a predetermined threshold. The results of the subtraction are stored as a new volumetric array $V_{def}$ that represents the defect in three dimensions.

Step 9: Grouping of Defect

The boundaries of the defect are defined by determining a minimum volume within the volumetric defect array $V_{def}$ that encompasses all of the difference data. This is accomplished by, for example, (1) defining the two-dimensional defect boundaries of each slice, using a conventional edge-detection technique, such as "automatic tracing" or "thresholding and skeletonization," and (2) combining the overlapping two-dimensional boundaries to form a three-dimensional boundary.

Step 10: Extraction of Defect Parameters

In addition to the defect parameters extracted in Step 7, the additional volume data may be used to provide important additional defect parameters. For example, defect parameters may be defined for the size, shape, reflectivity, transparency, and depth of a subsurface element.

Step 11: Defect Characterization

One or more subsurface defect parameters are added to the list of defect parameters used to define the defect-parameter vector. The defect-parameter vector is then compared, using conventional fuzzy logic techniques, with typical vectors for each known kind of defect. Based on this comparison, the ADC system characterizes the defect and estimates the probability that the selected characterization is accurate.

Because the extended defect-parameter vector contains additional and unique information, an ADC system in accordance with the present invention has the ability to identify and characterize subsurface defects. Moreover, because structures are created on a wafer over time, the depth parameter for a defect can provide an indication of the time in the process at which the defect occurred. Such timing information may prove invaluable in determining the source of a defect. The present invention thus provides functionality unavailable in conventional microscope image analysis.

IV. Three Dimensional Laser Confocal Phase Image ADC

In addition to laser confocal imaging, additional information and resolution, especially in microscopic surface and volume scanning, may be obtained by measuring the phase of reflected light. One unique method is Laser Feedback Interferometry (LFI), also called Laser Feedback Microscopy (LFM) or Laser Amplified Motion Detection and Analysis (LAMDA). In LFI, light reflected from a surface to be imaged reenters the laser cavity whence it originated. The reflected light is then subjected to the amplification provided by the laser gain mechanism, providing a unique method of detecting reflected light over a large dynamic range and with great precision.

Next, the phase difference $\Delta\phi$ and amplitude difference $\Delta I_\lambda$ is measured between the original and reflected light. The phase and amplitude difference data may be stored as arrays (e.g., $A_\phi(x, y, z, I_\lambda, \phi)$ or $A_\phi(x, y, I_\lambda, \phi)$). (Here $I_\lambda$ refers to the intensity ratio at a specific laser wavelength, $\lambda$. Lasers having multiple wavelengths may also be utilized, with an array for each wavelength taken either simultaneously or consecutively.)

All of the techniques described above for LIS volume, slice, and surface images may be extended to the LFM arrays and their derivatives, such as $A\phi(x, y, \phi)$. LFI/LFM/LAMDA technology has been described by Bearden, et. al. in a paper entitled *"Imaging and Vibrational Analysis with Laser-Feedback Interferometry,"* (University of California at Berkeley, Graduate Group in Biophysics and Division of Neurobiology, 1992.) The Bearden paper is incorporated herein by this reference.

Additional analytical information may be obtained with microscopic images, either conventional or confocal (or in combination), using techniques for obtaining white light or laser fluorescence images of the test and reference surfaces, techniques for obtaining laser Raman spectra of the defect/contaminant versus its background (both confocal and conventional), and a variety of special images in polarized light, darkfield illumination, phase contrast images, Differential Interference Contrast (DIC, also called Nomarski images), etc., each of which can provide additional parameters that can be associated with the confocal or confocal image arrays described above.

In the case of the three-dimensional volume image array as obtained with the LFM (or related combined microscope/interferometer combinations), the phase data provides an additional dimension for the array.

V. Three-Dimensional Laser Confocal Volume Image ADC Supplemented with Physical Analysis The ADC methods described above can identify many kinds of structural defects and the presence of contaminant particles or residue by analyzing physical attributes of the defect. Another embodiment of the invention provides additional information about the chemical composition of a defect. Such information often provides important clues as to the origin of a defect.

To analyze the chemical composition of a defect area, scattered laser light from the affected region may be automatically analyzed with a Raman spectrometer to identify both the Raman and/or fluorescence properties of the defect. (Fluorescence alone can be analyzed with optical filters and detectors, and does not require an optical spectrometer. Also, x-ray fluorescence, EDX, or related techniques may be performed in a scanning electron microscope (SEM) or similar instrument, providing additional composition information.)

Additional defect parameters are defined using one or more of the foregoing techniques to provide composition information. Using these parameters to calculate the defect-parameter vector further enhances defect discrimination.

VI. Conclusion

While the present invention has been described in connection with specific embodiments, variations of these embodiments will be obvious to those having ordinary skill in the art. For example, while the invention is described in connection with microscope that reflects a maximum intensity to the photodetector during a focused condition, it is clear that the invention may be modified to operate with a microscope that reflects a minimum intensity to the photodetector during a focused condition. Further, microscopes that do not utilize visible light, such as infrared, ion beam, or electron beam microscopes, could also benefit from the foregoing methods. Therefore, the spirit and scope of the appended claims should not be limited to the description of the preferred versions.

What is claimed is:

1. A method of locating defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume, the test surface being part of a semiconductor wafer;

determining, for each column of points specified by a unique x-y coordinate in the test volume, a maximum reflected intensity value of the focussed beam;

storing all the maximum reflected intensity values to form an array of test data representing a two-dimensional image of the test surface;

extracting a set of intensity test primitives from the intensity test data, the test primitives representing boundaries of features on the test surface; and comparing the set of intensity test primitives with a set of intensity reference primitives to determine whether the set of intensity test primitives is different from the set of intensity reference primitives.

2. The method of claim 1, wherein the test primitives are geometric constructs used to approximate features of the image of the test surface.

3. The method of claim 1, wherein the beam is radiated by a light source that provides at least one wavelength of laser light.

4. A method of locating defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn with each unique x-y-z coordinate within the test volume;

determining, for each column of points specified by a unique x-y coordinate in the test volume, a maximum reflected intensity value of the focussed beam;

storing all the maximum reflected intensity values to form an array of test data representing a two-dimensional image of the test surface;

extracting a set of intensity test primitives from the intensity test data, the test primitives representing boundaries of features on the test surface; and comparing the set of intensity test primitives with a set of intensity reference primitives to determine whether the set of intensity test primitives is different from the set of intensity reference primitives, wherein the set of intensity reference primitives is derived by scanning a reference surface in a reference volume with the focussed beam so that the focal point of the focussed beam coincides, in turn, with each unique coordinate within the reference volume, determining, for each column of points specified by a unique x-y coordinate, a maximum reflected intensity value of the focussed beam, storing all the maximum reflected intensity values in the reference volume as an array of reference data representing a two-dimensional image of the reference surface, and extracting the set of intensity reference primitives from the reference data.

5. A method of locating defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume, wherein the focused beam is radiated by a light source that provides white light;

determining, for each column of points specified by a unique x-y coordinate in the test volume, a maximum reflected intensity value of the focussed beam;

storing all the maximum reflected intensity values to form an array of test data representing a two-dimensional image of the test surface;

extracting a set of intensity test primitives from the intensity test data, the test primitives representing boundaries of features on the test surface; and comparing the set of intensity test primitives with a set of intensity reference primitives to determine whether the set of intensity test primitives is different from the set of intensity reference primitives.

6. A method of locating defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume;

determining, for each column of points specified by a unique x-y coordinate in the test volume, a maximum reflected intensity value of the focussed beam;

storing all the maximum reflected intensity values to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

determining, for each column of points specified by a unique x-y coordinate of the test volume, the z coordinate resulting in a maximum reflected intensity of the focussed beam;

storing all the locations along the z axes of all unique x-y coordinates to form a set of z test data representing a three-dimensional image of the test surface;

extracting a set of z test primitives from the z test data; and comparing the set of z test primitives with a set of z reference primitives to determine whether the set of z test primitives is different from the set of z reference primitives.

7. The method of claim 6, wherein the z test primitives are geometric constructs used to approximate z features of the three-dimensional image of the test surface.

8. The method of claim 6, wherein the beam is radiated by a light source that provides white light.

9. The method of claim 6, wherein the beam is radiated by a light source that provides at least one wavelength of laser light.

10. The method of claim 6, further comprising, the steps of:

storing all the reflected intensity values for all the unique x-y-z coordinates as a test volume array;

forming a defect volume array by comparing the test volume array to a reference volume array; and extracting defect parameters from the defect volume array.

11. The method of claim 6, wherein the set of z test primitives represents test image data and the set of z reference primitives represents reference image data, the method further comprising the step of aligning the test image data and reference image data relative to one another along the z axis.

12. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume, the test surface being part of a semiconductor wafer;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then generating intensity difference data from the difference between the set of intensity test primitives and the set of intensity reference primitives, extracting intensity defect parameters from the intensity difference data, the intensity defect parameters representing intensity differences between the image of the test surface and the image of a reference surface, and matching the intensity defect parameters with a knowledge base of intensity defect reference data;

determining, for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data;

comparing the set of z test primitives with a set of z reference primitives to determine whether the set of z test primitives is different from the set of z reference primitives;

if a difference exists between the set of z test primitives and the set of z reference primitives, then generating z difference data from the difference between the set of z test primitives and the set of z reference primitives, extracting z defect parameters from the z difference data, and matching the z defect parameters with a knowledge base of z defect reference data.

13. The method of claim 12, wherein the beam is radiated by a light source that provides at least one wavelength of laser light.

14. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn with each unique x-y-z coordinate within the test volume;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then
generating intensity difference data from the difference between the set of intensity test primitives and the set of intensity reference primitives,
extracting intensity defect parameters from the intensity difference data, the intensity defect parameters representing intensity differences between the image of the test surface and the image of a reference surface, and
matching the intensity defect parameters with a knowledge base of intensity defect reference data;

determining, for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data, the set of z test primitives representing test image data;

comparing the set of z test primitives with a set of z reference primitives to determine whether the set of z test primitives is different from the set of z reference primitives, the set of z reference primitives representing reference image data;

if a difference exists between the set of z test primitives and the set of z reference primitives, then
generating z difference data from the difference between the set of z test primitives and the set of z reference primitives,
extracting z defect parameters from the z difference data, and
matching the z defect parameters with a knowledge base of z defect reference data; and aligning the test image data and reference image data relative to one another along the z axis.

15. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then
generating intensity difference data from the difference between the set of intensity test primitives and the set of intensity reference primitives,
extracting intensity defect parameters from the intensity difference data, the intensity defect parameters representing intensity differences between the image of the test surface and the image of a reference surface, and
matching the intensity defect parameters with a knowledge base of intensity defect reference data;

determining, for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data, the z test primitives being geometric constructs used to approximate z features of the three-dimensional image of the test surface;

comparing the set of z test primitives with a set of z reference primitives to determine whether the set of z test primitives is different from the set of z reference primitives;

if a difference exists between the set of z test primitives and the set of z reference primitives, then
generating z difference data from the difference between the set of z test primitives and the set of z reference primitives,
extracting z defect parameters from the z difference data, and matching the z defect parameters with a knowledge base of z defect reference data.

16. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then generating intensity difference data from the difference between the set of intensity test primitives and the set of intensity reference primitives, extracting intensity defect parameters from the intensity difference data, the intensity defect parameters representing intensity differences between the image of the test surface and the image of a reference surface, and matching the intensity defect parameters with a knowledge base of intensity defect reference data;

determining, for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data;

comparing the set of z test primitives with a set of z reference primitives to determine whether the set of z test primitives is different from the set of z reference primitives;

if a difference exists between the set of z test primitives and the set of z reference primitives, then generating z difference data from the difference between the set of z test primitives and the set of z reference primitives, extracting z defect parameters from the z difference data, and matching the z defect parameters with a knowledge base of z defect reference data; and wherein the sets of intensity and z reference primitives are derived by scanning a reference surface in a reference volume with a focussed beam so that the focal point of the focussed beam coincides, in turn, with each unique x-y-z coordinate within the reference volume, determining, for each column of points specified by a unique x-y coordinate in the reference volume, a maximum reflected intensity value of the focussed beam, storing all of the maximum reflected intensity values for all of the unique x-y coordinates as an array of reference data representing a two-dimensional image of the reference surface, extracting a set of intensity reference primitives from the intensity reference data, determining, for each column of points specified by a unique x-y coordinate of the reference volume, the z coordinate resulting in a maximum reflected intensity of the focussed beam, storing all of the locations along the z axis of all of the points on the reference surface as a set of z reference data representing a three-dimensional image of the reference surface, and extracting a set of z reference primitives from the z reference data.

17. A method of characterizing defects on a test surface, wherein the test surface is contained within a test volume represented by a Cartesian coordinate system having x, y, and z axes describing a set of unique x-y-z coordinates the method comprising:

scanning the test surface in the test volume with a focussed beam so that the focal point of the focussed beam coincides, in turn, with each unique x-y-z coordinate within the test volume, wherein the focused beam is radiated by a light source that provides white light;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then generating intensity difference data from the difference between the set of intensity test primitives and the set of intensity reference primitives, extracting intensity defect parameters from the intensity difference data, the intensity defect parameters representing intensity differences between the image of the test surface and the image of a reference surface, and matching the intensity defect parameters with a knowledge base of intensity defect reference data;

determining for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data;

comparing the set of z test primitives with a set of z reference primitives to determine whether the set of z test primitives is different from the set of z reference primitives;

if a difference exists between the set of z test primitives and the set of z reference primitives, then
generating z difference data from the difference between the set of z test primitives and the set of z reference primitives,
extracting z defect parameters from the z difference data, and
matching the z defect parameters with a knowledge base of z defect reference data.

18. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume;

determining, for each column of points specified by a unique x-y coordinate in the test volume, a maximum reflected intensity value of the focussed beam;

storing all the maximum reflected intensity values for all the unique x-y coordinates to form an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then
generating intensity difference data from the difference between the set of intensity test primitives and the set of intensity reference primitives,
extracting intensity defect parameters from the intensity difference data, the intensity defect parameters representing intensity differences between the image of the test surface and the image of a reference surface, and
matching the intensity defect parameters with a knowledge base of intensity defect reference data;

determining, for each column of points specified by a unique x-y coordinate of the test volume, the z coordinate resulting in a maximum reflected intensity of the focussed beam;

storing all the locations along the z axis of all of the points on the test surface to form an array of z test data representing a three-dimensional image of the test surface extracting a set of z test primitives from the z test data;

comparing the set of z test primitives with a set of z reference primitives to determine whether the set of z test primitives is different from the set of z reference primitives;

if a difference exists between the set of z test primitives and the set of z reference primitives, then
generating z difference data from the difference between the set of z test primitives and the set of z reference primitives,
extracting z defect parameters from the z difference data, and
matching the z defect parameters with a knowledge base of z defect reference data;

storing all the reflected intensity values for all the unique x-y-z coordinates as a test volume array;

forming a defect volume array by comparing the test volume array to a reference volume array; and extracting defect parameters from the defect volume array.

19. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume, the test surface being part of a semiconductor wafer;

determining, for each column of points specified by a unique x-y coordinate in the test volume, a maximum reflected intensity value of the focussed beam;

storing all of the maximum reflected intensity values for all of the unique x-y coordinates as an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives; and if a difference exists between the set of intensity test primitives and the set of intensity reference primitives, then
generating difference data from the difference between the set of reference primitives and the set of test primitives,
extracting defect parameters from the difference data, and
matching the defect parameters with a knowledge base of defect reference data.

20. The method of claim 18, wherein the set of intensity reference primitives is derived by:

scanning a reference surface in a reference volume with a focussed beam so that the focal point of the focussed beam coincides, in turn, with each unique x-y-z coordinate within the reference volume;

determining, for each column of points specified by a unique x-y coordinate in the reference volume, a maximum reflected intensity value of the focussed beam;

storing all of the maximum reflected intensity values for all of the unique x-y coordinates as an array of reference data representing a two-dimensional image of the reference surface; and extracting a set of intensity reference primitives from the intensity reference data.

21. The method of claim 19, wherein the beam is radiated by a light source that provides at least one wavelength of laser light.

22. A method of characterizing defects on a test surface, wherein the test surface is contained within a test volume represented by a Cartesian coordinate system having x, y, and z axes describing a set of unique x-y-z coordinates, the method comprising:

scanning the test surface in the test volume with a focussed beam so that the focal point of the focussed beam coincides, in turn, with each unique x-y-z coordinate within the test volume;

determining, for each column of points specified by a unique x-y coordinate in the test volume, a maximum reflected intensity value of the focussed beam;

storing all of the maximum reflected intensity values for all of the unique x-y coordinates as an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives;

if a difference exists between the set of intensity test primitives and the set of intensity reference primitives, then
generating difference data from the difference between the set of reference primitives and the set of test primitives,
extracting defect parameters from the difference data, and
matching the defect parameters with a knowledge base of defect reference data; and wherein the set of intensity reference primitives is derived by
scanning a reference surface in a reference volume with a focussed beam so that the focal point of the focussed beam coincides, in turn, with each unique x-y-z coordinate within the reference volume,
determining, for each column of points specified by a unique x-y coordinate in the reference volume, a maximum reflected intensity value of the focussed beam,
storing all of the maximum reflected intensity values for all of the unique x-y coordinates as an array of reference data representing a two-dimensional image of the reference surface, and
extracting a set of intensity reference primitives from the intensity reference data.

23. A method of characterizing defects on a test surface, wherein the test surface is contained within a test volume represented by a Cartesian coordinate system having x, y, and z axes describing a set of unique x-y-z coordinates, the method comprising the steps of:

scanning, the test surface in the test volume with a focussed beam so that the focal point of the focussed beam coincides, in turn, with each unique x-y-z coordinate within the test volume, wherein the focussed beam is radiated by a light source that provides white light;

determining, for each column of points specified by a unique x-y coordinate in the test volume, a maximum reflected intensity value of the focussed beam;

storing all of the maximum reflected intensity values for all of the unique x-y coordinates as an array of test data representing a two-dimensional image of the test surface;

extracting a set of intensity test primitives from the intensity test data, the test primitives representing boundaries of features on the test surface;

comparing the set of intensity test primitives with a set of intensity reference primitives to determine whether the set of intensity test primitives is different from the set of intensity reference primitives; and if a difference exists between the set of intensity test primitives and the set of intensity reference primitives, then
generating difference data from the difference between the set of reference primitives and the set of test primitives, extracting defect parameters from the difference data, and matching the defect parameters with a knowledge base of defect reference data.

24. A method comprising the steps of:
generating three-dimensional microscope image data representing an object;
comparing the three-dimensional microscope image data to reference three-dimensional image data; and
characterizing the object based on the step of comparing;
wherein the step of characterizing includes determining the chemical composition of the object.

25. A method comprising the steps of:
generating three-dimensional microscope image data representing an object;
eliminating one dimension of the three-dimensional microscope image data to create two-dimensional microscope image data;
comparing the two-dimensional microscope image data to reference two-dimensional image data; and
characterizing the object based on the step of comparing.

* * * * *